United States Patent
Akiyama

[19]

[11] Patent Number: 6,093,292
[45] Date of Patent: Jul. 25, 2000

[54] ELECTROLYTE PRODUCING APPARATUS WITH MONITORING DEVICE

[75] Inventor: Osamu Akiyama, Chofu, Japan

[73] Assignees: Shimadzu Corporation, Kyoto; Water Research Institute, Tsukuba, both of Japan

[21] Appl. No.: 09/084,977

[22] Filed: May 28, 1998

[30] Foreign Application Priority Data

Jun. 17, 1997 [JP] Japan ................................. 9-176496

[51] Int. Cl.$^7$ ....................................................... C25B 9/00
[52] U.S. Cl. ................................ 204/263; 204/400
[58] Field of Search ........................... 204/252, 263, 204/400, 232

[56] References Cited

FOREIGN PATENT DOCUMENTS

| 0 612 694 | 8/1994 | European Pat. Off. . |
| 94/18543 | 8/1994 | WIPO . |

OTHER PUBLICATIONS

Patent Abstracts of Japan, vol. 016, No. 283 (C–0955), Jun. 24, 1992 & JP 04 074588 A (Matsushita Electric Works Ltd), Mar. 9, 1992.

Patent Abstracts of Japan, vol. 007, No. 142(p–205), Jun. 22, 1983 & JP 58 055839 A (Kawasaki Seitetsu KK), Apr. 2, 1983.

R Briggs, K.T.V. Grattan, Z. Mouaziz, A.F. Elvidge: "On–line monitoring of residual chlorine" Journal of Water Science and Technology, vol. 10, 1990, pp. 39–49, XP002099459 no month and year provided.

*Primary Examiner*—Kathryn Gorgos
*Assistant Examiner*—Thomas H Parsons
*Attorney, Agent, or Firm*—Kaensaka & Takeuchi

[57] ABSTRACT

An electrolyte producing apparatus is formed of an electrolyzing device for producing a strong acidic liquid on an anode side and a strong alkaline liquid on a cathode side through electrolyzing a basic liquid, a mixing device connected to the electrolyzing device for mixing a part of the acidic liquid and a part of the alkaline liquid to form a mixture of the acidic and alkaline liquids, and a measuring device including a light ejecting device for ejecting light to the mixture, and a light receiving device for receiving the light passing through the mixture. A light absorbance of the mixture is measured in an area of wavelengths of about 260 nm to 330 nm. A concentration of hypochlorous acid in the produced strong acidic liquid can be accurately monitored without using a coloring reagent to thereby obtain a pH value of the strong acidic liquid.

8 Claims, 6 Drawing Sheets mixing ratio of strong acidic liquid and strong alkaline liquid mixing ratio of strong acidic liquid and strong alkaline liquid

ELECTROLYTE PRODUCING APPARATUS WITH MONITORING DEVICE

BACKGROUND OF THE INVENTION

1. Field of the Invention

The present invention relates to an electrolyte producing apparatus used in a medical treatment industry, food industry and agricultural industry, more particularly an electrolyte producing apparatus with a monitoring device for monitoring a concentration of hypochlorous acid contained in a produced strong acidic liquid.

2. Description of the Related Art

The electrolyte producing apparatus is used to produce a strong acidic liquid on an anode side and a strong alkaline liquid on a cathode side by electrolyzing a chlorine-containing liquid. When the chlorine-containing liquid is electrolyzed, the strong acidic liquid produced on the anode side contains hypochlorous acid having a sterilizing ability. Especially, it is known that when a liquid containing sodium chloride and potassium chloride is subjected to electrolysis, the strong acidic liquid produced on the anode side contains several tens ppm of hypochlorous acid, and shows a low pH value of 2.5–3.0 and a high oxidation-reduction potential (hereinafter referred to as ORP) of +1,100 mV to thereby possess a strong sterilizing effect.

Thus, in the medical treatment industry, the produced strong acidic liquid is used for disinfecting hands and sterilizing MRSA causing infection in a hospital. Also, the produced strong acidic liquid is used for disinfecting and sterilizing kitchen apparatus in the food industry; and sterilizing fishes and germs, e.g. 0–157, in the processed marine product industry. Further, in the agricultural industry, a strong acidic liquid obtained by electrolyzing a liquid containing potassium chloride is used for disinfecting pathogenic bacteria in a house cultivation for melons, vegetables, pears, flowers and the like, and sterilizing unhulled rices, so that use of agricultural chemicals can be reduced.

However, in the conventional electrolyte producing apparatus, it is difficult to confirm whether the strong acidic liquid having sterilizing effects is produced or not. Therefore, even if a predetermined strong acidic liquid is not obtained, there is a risk of using an insufficient acidic liquid. In case the strong acidic liquid is used for physical safety and hygiene, such as sterilization and disinfection, it is important to obtain the strong acidic liquid with an accurate concentration.

The concentration of hypochlorous acid in the produced strong acidic liquid having the sterilizing ability naturally varies according to a characteristic, temperature, pH value of used tap water or pure water, and production quantity of the strong acidic liquid per unit hour. However, a user does not notice such variation. Of course, it is possible to measure a concentration by mixing the strong acidic liquid produced on the anode side with a coloring reagent, such as orthotolidine, separately prepared outside the apparatus. However, this method includes a laborious management and maintenance, such as exchange and supply of the reagent, which results in an increased cost.

BRIEF SUMMARY OF THE INVENTION

In view of the above, an object of the present invention is to provide an electrolyte producing apparatus, wherein a concentration of hypochlorous acid in the strong acidic liquid can be monitored without the laborious management and maintenance.

Another object of the present invention is to provide an electrolyte producing apparatus as stated above, wherein the concentration of hypochlorous acid can be measured accurately and economically.

Further objects and advantages of the invention will be apparent from the following description of the invention.

In order to solve the above problems, according to a first aspect of the present invention, an electrolyte producing apparatus comprises an electrolyzing device for producing a strong acidic liquid on an anode side and a strong alkaline liquid on a cathode side by electrolyzing a chlorine containing liquid; mixing means or system for mixing a part of the strong acidic liquid produced on the anode side and a part of the strong alkaline liquid produced on the cathode side; and a measuring device for measuring an absorbance of light in an area of wavelengths of substantially 260 nm to 330 nm, of the mixed liquid.

According to a second aspect of the present invention, the mixing device of the above-mentioned electrolyte producing apparatus mixes a part of the produced strong acidic liquid and a part of the produced strong alkaline liquid at a mixing ratio such that hypochlorous acid contained in the strong acidic liquid is substantially completely dissociated into $H^+$ ion and hypochlorous acid ion. The above apparatus is further provided with a calculating or operating device for conducting a dilution-correction calculation with respect to the above-measured light absorbance data by using a correction factor corresponding to the above mixing ratio.

According to a third aspect of the present invention, in the electrolyte producing apparatus as stated above, the mixing system includes a two-tank type first open-air liquid tank into which a part of the produced strong acidic liquid and a part of the produced strong alkaline liquid are introduced, respectively; a second open-air type liquid tank into which supernatant liquids of the respective tanks of the first open-air type liquid tank are introduced; and a device for introducing a supernatant liquid of the second open-air type liquid tank into the above-mentioned measuring device.

Chlorine becomes a balanced state of chlorine (molecule) and hypochlorous acid (HClO) when a pH value is smaller than 5 as shown in the following chemical formula (1); and becomes a balanced state of hypochlorous acid and minus ion of hypochlorous acid when a pH value is larger than 5 as shown in the following chemical formula (2).

$$Cl_2 + H_2O \leftrightharpoons HClO + H^+ + Cl^- \tag{1}$$

$$HClO \leftrightharpoons H^+ + OCl^- \tag{2}$$

On the other hand, hypochlorous acid ion shows a characteristic absorption to create a peak in the vicinity of a wavelength of 292 nm of a light absorption spectrum.

Therefore, even if hypochlorous acid is contained in the strong acidic liquid produced on the anode side, hypochlorous acid does not exist as the hypochlorous acid ion due to the strong acidity, and as it is, light absorption does not take place in the vicinity of the wavelength of 292 nm. On the contrary, when the strong alkaline liquid produced on the cathode side is added to the strong acidic liquid, hypochlorous acid is dissociated to hypochlorous acid ion since the pH value is increased.

Therefore, in case a part of the strong acidic liquid produced on the anode side and a part of the strong alkaline liquid produced on the cathode side are mixed, and a light absorption intensity in an area of wavelengths of about 260 nm to 330 nm is measured with respect to the mixed liquid, there can be measured a concentration of hypochlorous acid ion having a characteristic absorption with a peak in the vicinity of the wavelength of 292 nm, in other words, a concentration of hypochlorous acid in the strong acidic liquid before the alkaline liquid is mixed thereto. Since the concentration of hypochlorous acid contained in the strong acidic liquid produced on the anode side is measured by utilizing the strong alkaline liquid produced on the cathode side, a coloring reagent is not required, and labor and cost can be reduced.

Further, in case the strong acidic liquid and the strong alkaline liquid are mixed at a ratio having a pH value such that hypochlorous acid is completely dissociated to hypochlorous acid ion, the measured light absorbance data in the vicinity of the wavelength of 292 nm accurately corresponds to the concentration of hypochlorous acid. However, since the strong acidic liquid is diluted with the strong alkaline liquid, the obtained data can be converted to the original concentration of hypochlorous acid in the strong acidic liquid by correction with a diluting ratio correcting factor corresponding to the mixing ratio. Thus, the concentration of hypochlorous acid in the strong acidic liquid produced on the anode side can be accurately monitored.

Also, the produced acidic liquid contains a chlorine gas and an oxygen gas, and the produced alkaline liquid contains a hydrogen gas. Namely, both liquids are gas-liquid mixtures. Further, tap water as water to be measured contains salts of calcium carbonate, magnesium carbonate and silica existing therein, and these salts precipitate as a result of electrolysis and float in the produced alkaline liquid. In case a light absorption intensity of the mixture of the acidic liquid and the alkaline liquid is measured, since a transmitted light quantity varies due to scattering of light if bubbles exist in the mixture, an accurate measuring result can not be obtained. Also, substances precipitated in the liquid adhere to a cell window as stains to thereby deteriorate a measuring accuracy.

However, the bubbles vary in the diameters from a maximum length of 10 mm to a length shorter than 1 mm, and the precipitates vary from a large size liable to settle or accumulate to a small size hard to settle.

Thus, two step processes including a first liquid tank and a second liquid tank solve the problems effectively. More specifically, as the first liquid tank, a two-tank type open-air liquid tank is employed, wherein the produced acidic liquid and alkaline liquid are introduced into the respective tanks of the first liquid tank, and the supernatant liquids thereof are taken out, so that large bubbles are released into the atmosphere, and the large precipitated substances are settled and removed.

As the second step, after the two taken-out supernatant liquids are mixed, the mixture is introduced into the second open-air type liquid tank, and a supernatant liquid in the second open-air type liquid tank is then introduced into the measuring device. Since the liquid introduced into the second liquid tank has been in a balanced state in an atmosphere in the first step, small bubbles contained in the liquid can be easily released or removed into the atmosphere in the second liquid tank. Also, since the small precipitated substances are settled or accumulated in the second liquid tank, the small precipitates can be easily removed by taking out the supernatant liquid therefrom. Namely, the liquid, from which bubbles and precipitates are substantially removed, can be obtained.

DETAILED DESCRIPTION OF PREFERRED EMBODIMENTS

Figure 1:
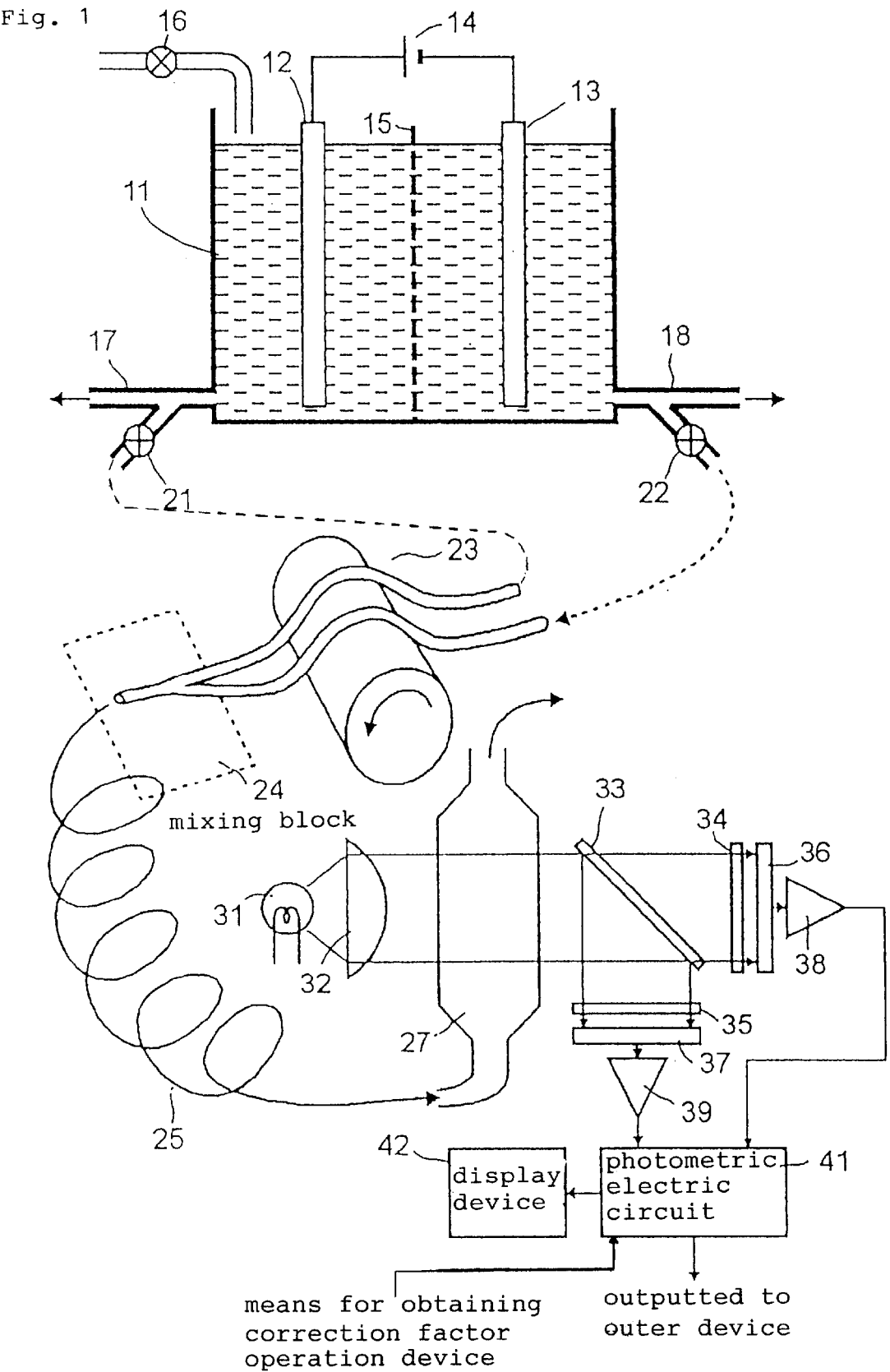
FIG. 1 is a diagram showing an electrolyte producing apparatus of an embodiment according to the present invention.

Embodiments of the present invention will be explained with reference to the accompanying drawings. In FIG. 1, an electrolytic vessel 11 contains tap water having about 20 mM (millimole) of sodium chloride, in the present embodiment, through a valve 16, and is provided with a DC voltage source 14 disposed between an anode 12 and a cathode 13 to sandwich an ion exchange membrane 15. A strong acidic liquid produced on a side of the anode 12 is taken out through a strong acidic liquid discharge port 17, and a strong alkaline liquid produced on a side of the cathode 13 is taken out through a strong alkaline liquid discharge port 18. These liquids are used for conventional purposes, such as sterilization and washing. Further, the respective discharge ports 17 and 18 are provided with measuring branches, so that a part of the strong acidic solution and a part of the strong alkaline solution can be taken out through valves 21 and 22, respectively.

The respective branches are connected to a squeezing pump 23 through vinyl chloride type tubes, and the strong acidic liquid and the strong alkaline liquid are fed by the squeezing pump 23, respectively. The two liquids pass through a mixing block 24 and a mixing coil 25, or a flow cell introducing path system, so that they are sufficiently mixed and homogenized; then fed to a flow cell 27 made of quartz glass; and discharged.

An irradiation optical system and a measuring optical system are disposed to sandwich the flow cell 27 therebetween. The irradiation optical system includes a light source 31, such as a tungsten lamp and deuterium lamp, and a light-gathering optical system 32, such as a lens and mirror. A light beam irradiated from the irradiation optical system passes through the flow cell 27 and measured by the measuring optical system. First, the light beam is divided into two by a beam splitter 33, such as a quartz plate, and the split light beams pass through optical filters 34, 35 to be detected by photocells 36, 37, respectively. One optical filter 34 is formed of an interference filter having a main transmission wavelength of 292 nm, and the other optical filter 35 is formed of a band-pass filter or sharp-cut filter transmitting light with the wavelengths longer than 400 nm.

The photocells 36, 37 are formed of, for example, Si photocell or the like, and detected signals, i.e. electric signals, are applied to a photometric electric circuit 41 through preamps 38, 39, respectively. In the photometric electric circuit 41, the detected signals are converted into signals for light absorbance, and an operation for obtaining a difference between the two light absorbance and an operation for converting the difference into a concentration of hypochlorous acid are carried out. In other words, the difference between the light absorbance with respect to light having a wavelength of 292 nm and the light absorbance with respect to light having a wavelength longer than 400 nm is obtained. The difference between the light absorbance is converted into the concentration of hypochlorous acid by being multiplied with a correction factor corresponding to a mixing ratio, and the concentration is displayed on a display device 42. Also, the concentration data can be outputted to an outer device, such as a printer and controlling device, if required.

Thus, the concentration of hypochlorous acid is accurately displayed and outputted.

Figure 2:
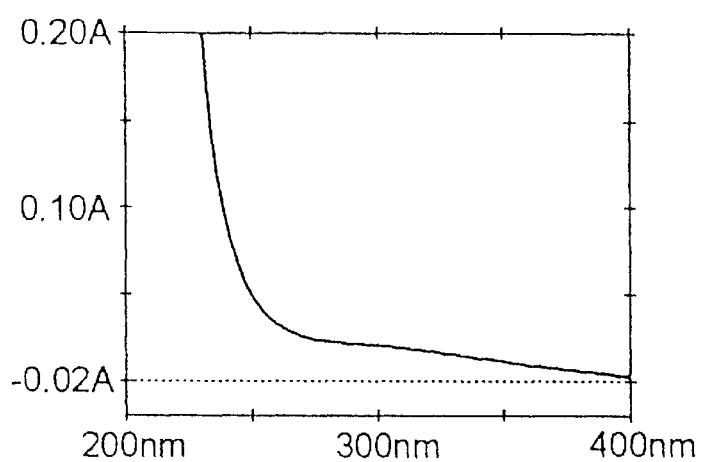
FIG. 2 is a graph showing a light absorption spectrum of a strong acidic liquid produced on an anode side.
Figure 3:
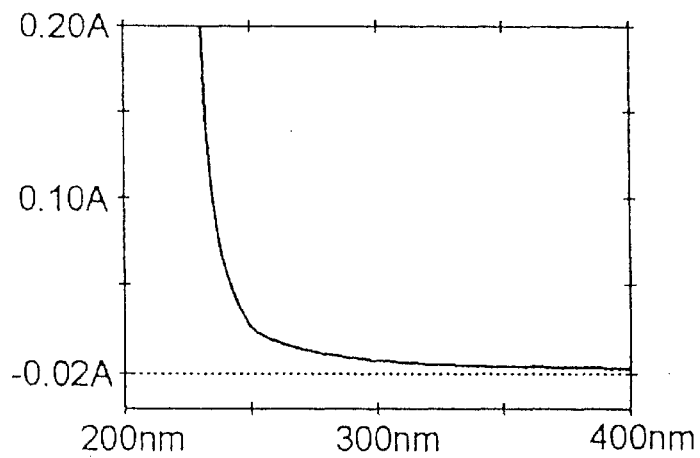
FIG. 3 is a graph showing a light absorption spectrum of a strong alkaline liquid produced on a cathode side.

More specifically, first, absorption spectrum of only the strong acidic liquid, where the strong alkaline liquid is not mixed therein, produced on the side of the anode 12 is measured by a separately prepared absorption meter, to thereby obtain a result as shown in FIG. 2. Also, an absorption spectrum of only the strong alkaline liquid produced on the side of the cathode 13 is measured in the same manner as mentioned above, to thereby obtain a result as shown in FIG. 3. Further, an absorption spectrum of a mixture of the strong acidic liquid and the strong alkaline liquid at a mixing ratio of 1:2 is measured, to thereby obtain a result shown in FIG. 4.

In the spectrum shown in FIG. 2, although a weak shoulder portion can be observed in an ultraviolet area, a absorption peak can not be observed. Also, in the spectrum shown in FIG. 3, no characteristic absorption can be observed in the ultraviolet area. On the other hand, as shown in FIG. 4, the above mixed liquid shows a characteristic absorption having a peak in the vicinity of 292 nm.

Figure 5:
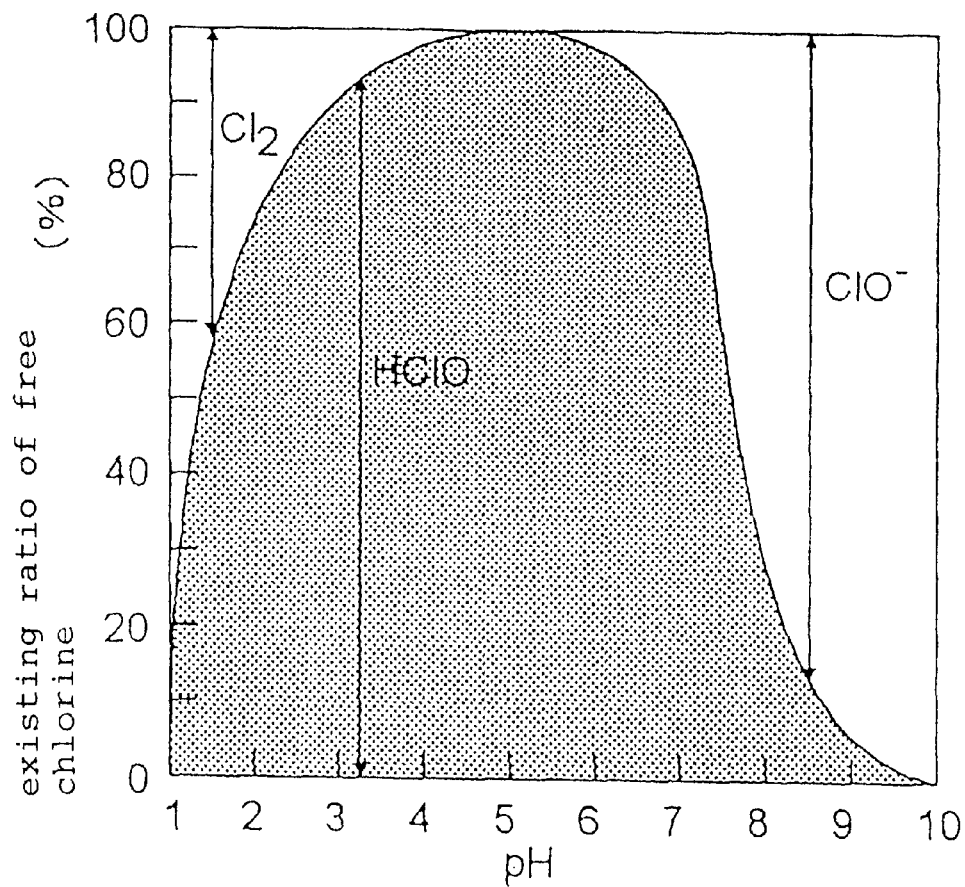
FIG. 5 is a graph showing existing ratio of free chlorine with respect to a pH value.

It is known that a ratio showing existence of free chlorine varies according to a pH value, as shown in FIG. 5. Since the strong acidic liquid at the time of production shows a pH value of 2.5–3.0, according to FIG. 5, free chlorine exists therein mainly as hypochlorous acid, and a part thereof exists as a chlorine molecule (refer to Chemical Formula 1). This state also can be seen from the absorption spectrum shown in FIG. 2 with respect to the strong acidic liquid. In other words, hypochlorous acid and chlorine do not have the characteristic absorption in the ultraviolet area.

Figure 6:
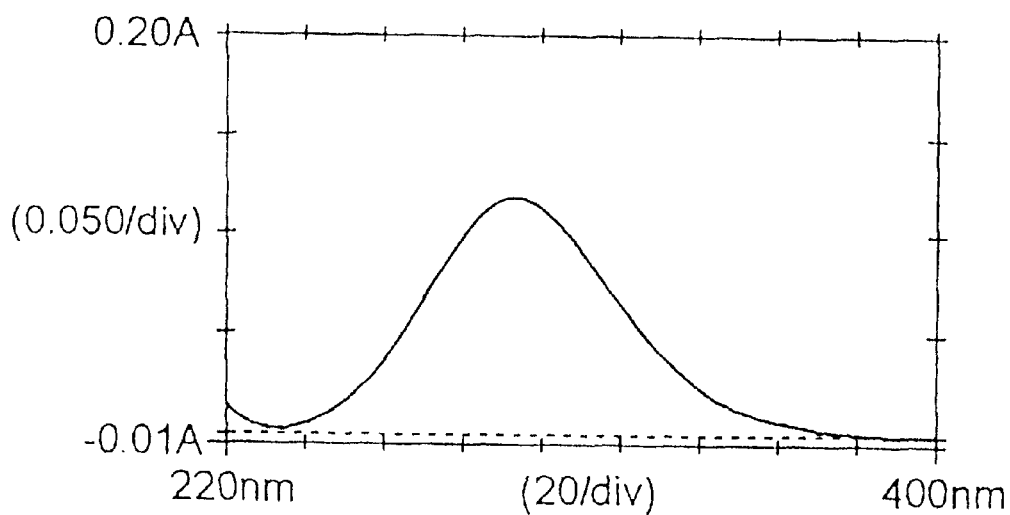
FIG. 6 is a graph showing a light absorption spectrum of an antiformin aqueous solution.

On the contrary, hypochlorous acid ion existing in a liquid having a pH value over 6–7 (refer to Chemical Formula 2) has an absorption peak in the vicinity of the wavelength of 292 nm. In order to confirm this, an aqueous solution of antiformin, i.e. sodium hypochlorite NaClO, is prepared separately, and an absorption spectrum is measured. The result is shown in FIG. 6. From FIG. 6, it is considered that the absorption peak in the vicinity of the wavelength of 292 nm in an ultraviolet area is apparently a characteristic absorption of hypochlorous acid ion dissociated from sodium hypochlorite, judging from the fact that the material is an aqueous solution of a pure product of antiformin.

Figure 4:
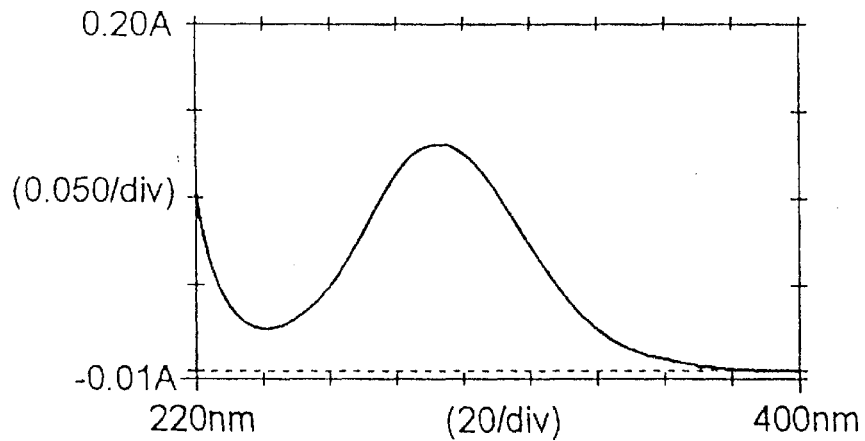
FIG. 4 is a graph showing a light absorption spectrum of a mixture obtained by mixing the strong acidic liquid and the strong alkaline liquid at a rate of 1:2.

Thus, when FIGS. 4 and 6 are compared, it is found that the curves show good coincidence having absorption peaks themselves in the vicinity of 292 nm except that spectrum shapes are slightly different, i.e. notch depths in the vicinity of 230–240 nm are different. From this fact, it is assumed that when the strong acidic liquid and the strong alkaline liquid are mixed at a ratio of 1:2, the pH value is changed; hypochlorous acid is dissociated into plus hydrogen ion and minus ion of hypochlorous acid; and the hypochlorous acid ion causes the absorption peak to thereby obtain the spectrum as shown in FIG. 4.

The only problem is whether the absorption peak in the vicinity of the wavelength of 292 nm accurately shows the concentration of hypochlorous acid of the strong acidic liquid before the strong alkaline liquid is mixed therewith. More specifically, according to FIG. 5, in case a pH value of the mixed liquid is smaller than 10, since hypochlorous acid and hypochlorous acid ion exist together, a measurement of absorption by the hypochlorous acid ion does not mean the concentration of hypochlorous acid itself before dissociation. On the other hand, in case the pH value of the mixed liquid is larger than 10, since hypochlorous acid is all dissociated into hypochlorous acid ion, a measured value accurately corresponding to the concentration of hypochlorous acid can be obtained by measuring an ultraviolet absorbance at the wavelength of 292 nm.

Figure 7:
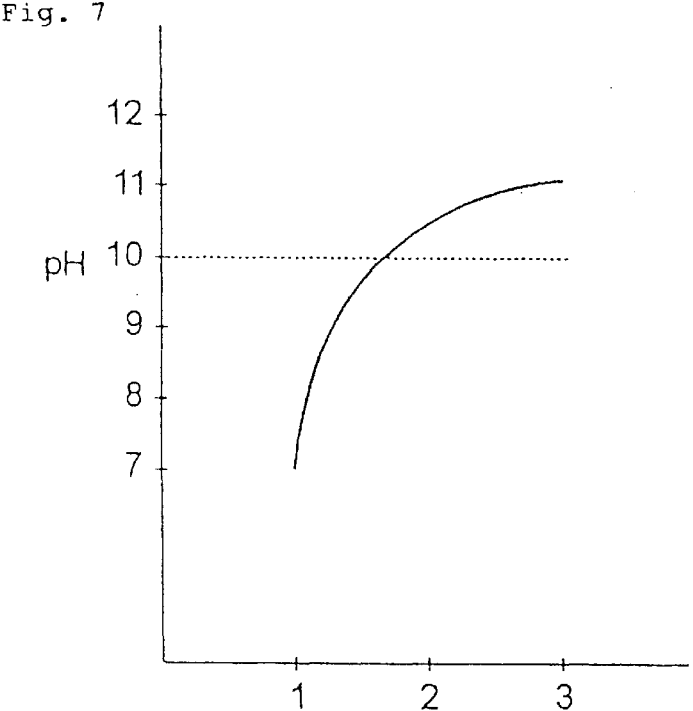
FIG. 7 is a graph showing a relationship between a mixing ratio of the strong acidic liquid and the strong alkaline liquid and a pH value.

Next, a relationship between a mixing ratio of the mixed liquid and its pH value is measured to obtain a result shown in FIG. 7. According to FIG. 7, the pH value is larger than 10 in the vicinity of the mixing ratio of 1:1.65 and the pH value is 10.4 at the mixing ratio of 1:2, so that the mixed liquid has a pH value enough to dissociate all the hypochlorous acid in the mixed liquid into hypochlorous acid ion. Therefore, as explained in the above embodiment, there is a sufficient reason of mixing at a rate of 1:2.

Figure 8:
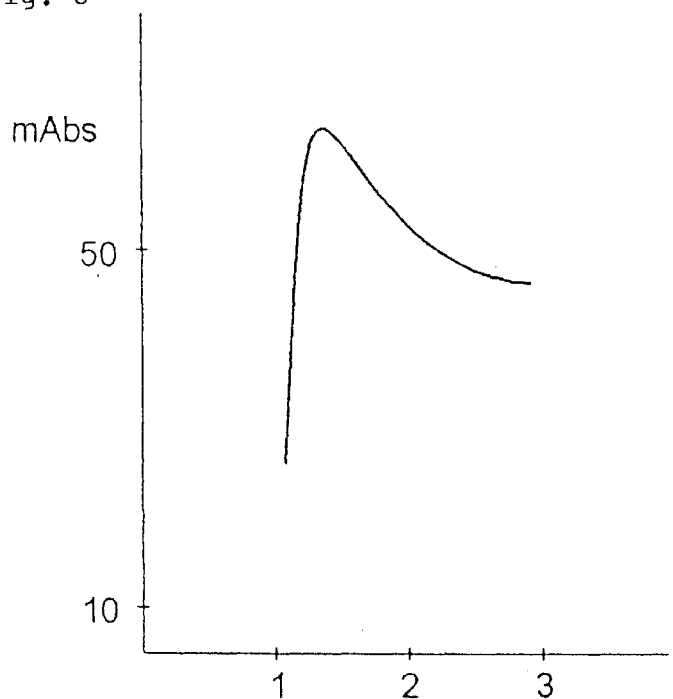
FIG. 8 is a graph showing a relationship between a mixing ratio of the strong acidic liquid and the strong alkaline liquid and light absorbance at a wavelength of 292 nm.

Further, a relationship between the concentration of hypochlorous acid with respect to the produced strong acidic liquid and an ultraviolet absorbance at a wavelength of 292 nm when the strong acidic liquid is diluted with the strong alkaline liquid, is examined. FIG. 8 shows a measurement result of light absorbance at the wavelength of 292 nm when a mixing ratio of the strong acidic liquid and the strong alkaline liquid is changed from 1:1 to 1:3. The measured value of the light absorbance is a value obtained by subtracting an absorbance over a wavelength of 400 nm from an absorbance at a wavelength of 292 nm, as in the embodiment shown in FIG. 1.

With respect to several mixing ratios, corrected absorbance corresponding to measured values of absorbance differences and diluting ratios are shown in the following Table. In other words, when the strong acidic liquid is mixed with the strong alkaline liquid, although hypochlorous acid in the mixed liquid is progressively dissociated to hypochlorous acid ion, since the mixture is also diluted and its apparent concentration becomes weak, it is required to correct the concentration with a correction factor corresponding to the diluting ratio.

TABLE

| mixing ratio | absorbance difference (mAbs) | diluting ratio correction factor | corrected absorbance |
| --- | --- | --- | --- |
| 1:1.5 | 69.5 | (1 + 1.5) / 1 = 2.5 | 174 |
| 1:2 | 57.5 | (1 + 2) / 1 = 3 | 173 |
| 1:3 | 43.0 | (1 + 3) / 1 = 4 | 172 |

From the above table, the corrected absorbance are 173±1 mAbs, which shows an excellent coincidence. Further, the table shows that since in the mixing ratio of 1:1.5, all hypochlorous acid has already been dissociated into hypochlorous acid ion, even if the mixing ratio is further increased, the strong acidic liquid is simply diluted by the strong alkaline liquid, and the number of the hypochlorous acid ion is substantially constant. More specifically, in case the strong alkaline liquid is mixed with the strong acidic liquid to increase the pH value in a situation where hypochlorous acid is completely dissociated into hypochlorous acid ion, a correct absorbance in proportion to an ion quantity of hypochlorous acid can be obtained by simply multiplying the measured result with a correction factor corresponding to the mixing ratio. Namely, the concentration of hypochlorous acid ion can be found, and finally, the concentration of hypochlorous acid in the produced strong acidic liquid before the strong alkaline liquid is mixed therein can be accurately obtained.

Incidentally, the above measured results and values are obtained under the specific conditions, but the invention should not be limited thereto. In the above, although the mixing ratios of 1:1.5 and 1:2 are good values, they are only applied to a case where tap water containing NaCl as an electrolytic assistant is used as raw water. These values may vary in case KCl is used as the electrolytic assistant, well water is used instead of tap water, or electrolytic conditions are different.

In the above embodiment, the light absorbance at the wavelength of 292 nm showing a characteristic absorption peak of hypochlorous acid ion and the light absorbance over the wavelength of 400 nm where no absorption is carried out are measured, and a difference between the measured values is calculated, so that the measurement with less errors can be carried out. More specifically, in a different light absorption method, in case a slight suspension is formed or fine bubbles are generated in the mixed liquid, or the flow cell 27 is stained, influences of increasing a background level of the light absorbance can be prevented. However, in case an accurate measurement is not required, the above explained process can be simplified, and only a measurement at the wavelength of 292 nm is sufficient. In case only one wavelength is measured, just one optical system for the measurement is enough. Thus, a structure of the electrolyte producing apparatus can be simplified, which results in a reduced production cost.

Figure 9:
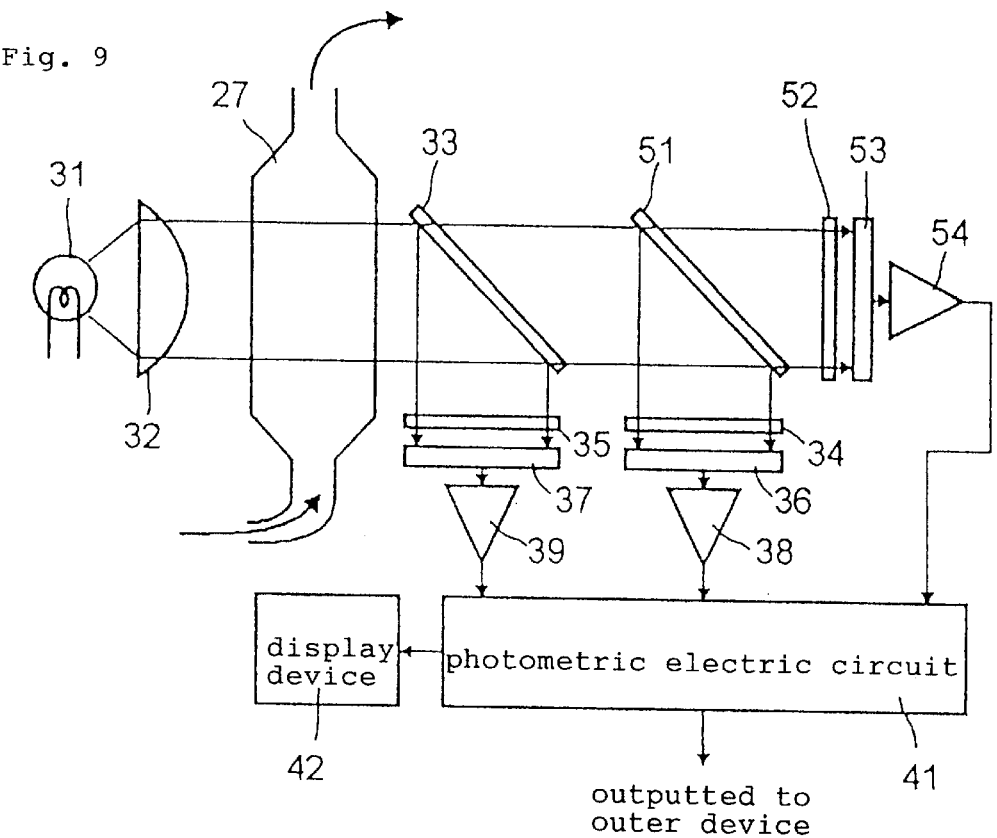
FIG. 9 is a block diagram showing a part of another embodiment according to the present invention.

On the contrary, in case three wavelengths are measured, the accuracy can be further increased when compared with the case where two wavelengths are measured. In this case, the measurement optical system for measuring light transmitted through the flow cell 27 shown in FIG. 1 is changed to a structure as shown in FIG. 9. More specifically, in addition to a wavelength 292-nm measuring system including the optical filter 34, photocell 36 and preamp 38 for transmitting light in the vicinity of the wavelength of 292 nm and a wavelength 400-nm measuring system including the optical filter 35, photocell 37 and preamp 39 for transmitting light having the wavelength over 400 nm, there are provided another beam splitter 51, and an optical filter 52, photocell 53 and preamp 54 for transmitting light in the vicinity of a wavelength of 240 nm to thereby measure light of the wavelength of 240 nm.

Figure 10:
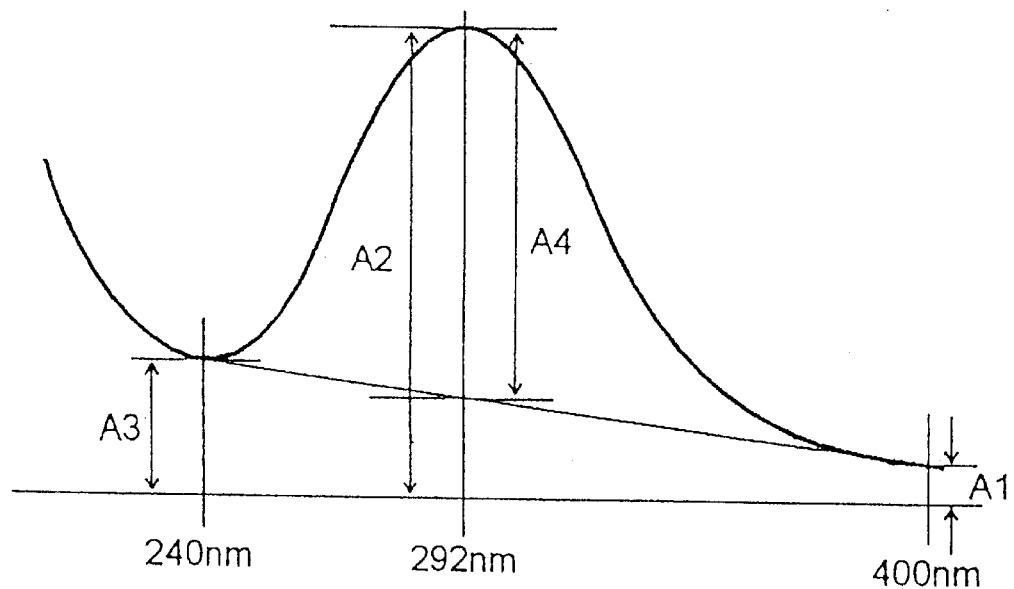
FIG. 10 is a graph explaining a correction theory in case three wavelengths are measured.

Since a measured value A3 shows a light absorbance in a wavelength area which forms a bottom portion of the light absorption spectrum shown in FIG. 4, as shown in FIG. 10, in addition to an absorbance A1 in the wavelength area over 400 nm and an absorbance A2 at the absorption peak of the wavelength 292 nm, the absorbance A3 at the bottom in the vicinity of the wavelength of 240 nm can be obtained. These values are inputted to the photometric electric circuit 41, and the following operation is carried out.

$$A4 = A2 - \{(400-292)A3 + (292-240)A1\}/(400-240)$$

$$= A2 - (108 \cdot A3 + 52 \cdot A1)/160$$

$$= A2 - 0.68 \cdot A3 - 0.33 \cdot A1$$

The value A4 thus obtained, as can be seen from FIG. 10, is a value obtained by accurately removing a background value from the measured value A2 of the light absorbance at the wavelength of 292 nm.

Also, since a light absorbance to be measured is not limited to the wavelength of 292 nm, provided that sensitivity may slightly be sacrificed, a light absorbance in a wavelength area of 260 nm to 330 nm may be detected.

In the above, although it is described that the light absorbance in the vicinity of the wavelength of 292 nm is corrected by a diluting ratio, the following correction factors may be added thereto. As can be seen from the curves shown in FIGS. 4 and 6, shapes of the absorption spectrum of a mixture of the electrolytes and the absorption spectrum of an aqueous solution of sodium hypochlorite are slightly different, and the difference resides in notch depths at the bottom peaks in the vicinity of the wavelengths of 230 nm to 240 nm. The present inventor noticed that the difference resides in that the electrolyte is made by adding NaCl (generally available product is used) to tap water, so that fine impurities exist therein, while an aqueous solution of sodium hypochlorite does not contain such fine impurities.

Thus, in addition to the diluting ratio correction factor, if a correction factor for correcting the influence by the small amount of the impurities is introduced therein, more accurate measurement can be obtained. For this purpose, it is considered that either of the following two equations is carried out. In other words, a fixed coefficient K2, for example 0.95, is multiplied, or a fixed value A', for example 10 mAbs, is deducted.

$$B = A4 \cdot K1 \cdot K2 \cdot \epsilon$$

$$B = (A4 - A') \cdot K1 \cdot \epsilon$$

wherein B represents a concentration of hypochlorous acid; A4 represents a value obtained by the two wavelength method, i.e. a value obtained by subtracting a value at the wavelength of 400 nm from a value at the wavelength of 292 nm, or the value obtained by the three wavelength method (refer to the above equations); K1 represents a diluting ratio correction factor; and $\epsilon$ represents a molar light absorption coefficient.

Figure 11:
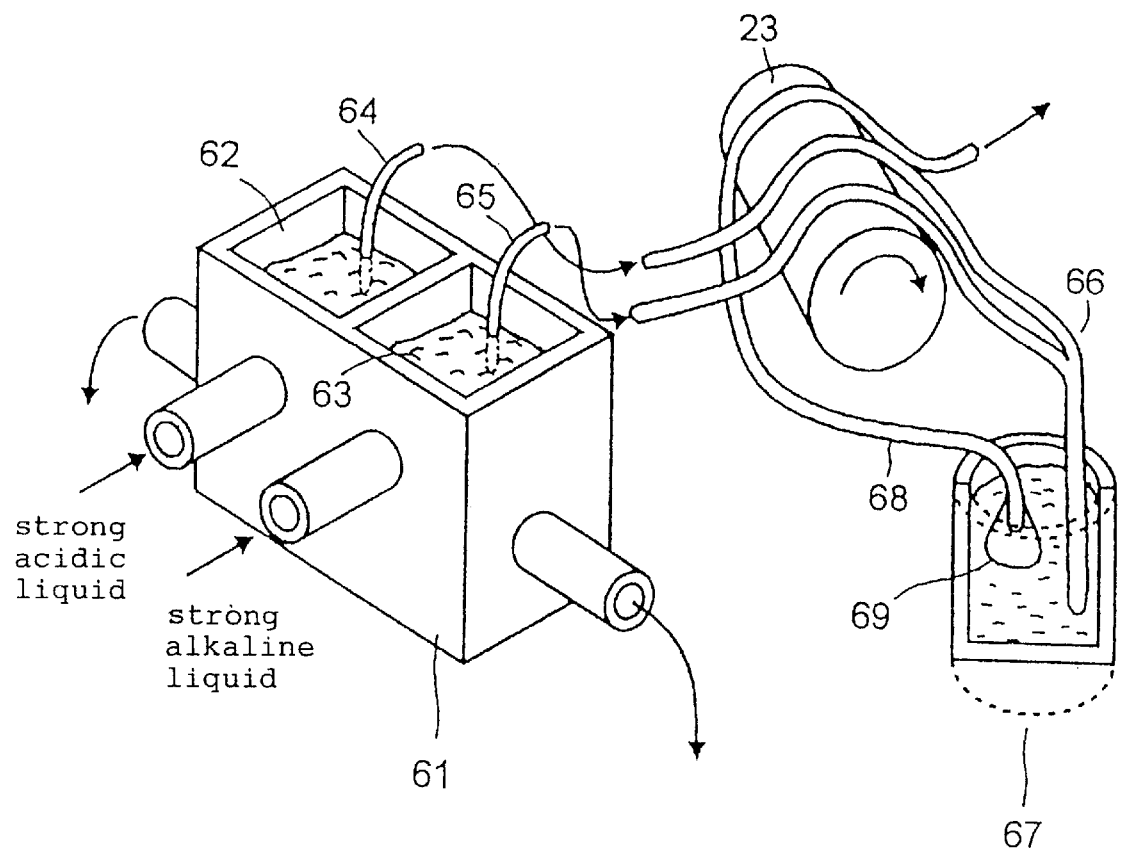
FIG. 11 is a diagram showing an embodiment of an improved liquid mixing-introducing system.

FIG. 11 shows an example of an improved liquid mixing introducing system for mixing the produced strong acidic liquid and strong alkaline liquid and introducing the mixture into a measuring system based on the two wavelength method or the three wavelength method. In FIG. 11, a first liquid tank 61 and a second liquid tank 67 are of an open-air type. The strong acidic liquid and the strong alkaline liquid produced at the electrolytic vessel 11 are first introduced into the first liquid tank 61, and then introduced into the second liquid tank 67 after they are mixed in a Y-character shape mixer 66. The first and second liquid tanks 61 and 67 are made of a vinyl chloride type material in view of acid resistance with respect to the acidic liquid.

The first liquid tank 61 is of a two tank type including independent liquid tanks 62 and 63 having wide open-air areas, i.e. upper surfaces, respectively. The liquid tanks 62 and 63 are provided with introduction ports and discharge ports, respectively. The strong acidic liquid and the strong alkaline liquid are introduced through the respective introduction ports to be stored therein once, and then discharged through the discharge ports provided in the vicinity of bottoms, respectively. The liquid tanks 62 and 63 may be, for example, of square columns having bottoms of a 100 mm square, respectively.

The strong acidic liquid produced at the electrolytic vessel 11 contains a chlorine gas and an oxygen gas, while the strong alkaline liquid contains a hydrogen gas. Thus, both of them are gas-liquid mixtures, respectively, containing a large amount of gas. Further, tap water to be measured contains dissolved salts of calcium carbonate, magnesium carbonate and silica. These are precipitated as the result of electrolysis and float in the produced alkaline liquid. Bubbles in the liquids vary in the size from a diameter smaller than 1 mm to a diameter of 10 mm. The precipitates also vary from a large size liable to settle to a small size unable to settle.

The strong acidic liquid and the strong alkaline liquid are introduced from the electrolytic vessel 11 under a pressure near raw water, such as tap water, into the liquid tanks 62, 63 having the wide open-air areas in their upper surfaces, and are stored once therein, so that the pressures are returned to the atmospheric pressure. Therefore, large bubbles having the diameters of 2 mm to 10 mm are immediately broken and gases enclosed in the bubbles are released in the atmosphere. Also, heavy salts among the precipitated salts, such as calcium carbonate, in the strong alkaline liquid, which are liable to settle are settled or accumulated on a bottom of the liquid tank 63.

Then, absorption or transfer tubes 64, 65 are inserted into the liquid tanks 62, 63, respectively, to absorb the supernatant liquids, so that the strong acidic liquid and the strong alkaline liquid from which large bubbles and precipitates have been removed can be taken out. The absorption tubes 64, 65 absorb the strong acidic liquid and the strong alkaline liquid at a fixed flow rate, respectively, by a squeezing pump 23 as shown in the drawing, and transfer them to a Y-character shape mixer 66 to mix them at a fixed rate. The mixed liquid is introduced to a bottom portion of the second liquid tank 67. The second liquid tank 67 is of an open-air type in its upper surface as in the first liquid tank 61, and is disposed such that a forward end of an absorption or transfer tube 68 provided with a filter 69 is located in the vicinity of the center thereof. The absorption tube 68 absorbs the mixed liquid through the squeezing pump 23, and transfers it to a flow cell 27 (refer to FIGS. 1 and 9) of an optical measuring system.

Although the strong acidic liquid and the strong alkaline liquid in the first liquid tank 61 contain therein many small bubbles having the diameters smaller than 1 mm, while passing through the absorption tubes 64 and 65, these bubbles are combined together, so that the bubbles grow to have the diameters of about 1 to 2 mm. Also, the strong alkaline liquid contains therein fine precipitated salts and the like. Although the mixed liquid contains these bubbles and the fine precipitated salts, since the mixed liquid is introduced to the bottom portion of the second liquid tank 67, the bubbles can be released in the atmosphere and the precipitated salts and the like can be settled. Thus, by taking the supernatant liquid by the absorption tube 68, the relatively small bubbles and precipitated salts and the like can be removed.

In this embodiment, since the forward end of the absorption tube 68 is provided with the filter 69 with a small mesh, the bubbles and the precipitated salts and the like can be surely prevented from being sucked into the absorption tube 68. More specifically, since the strong acidic liquid and the strong alkaline liquid to be sucked by the absorption tubes 64 and 65 is in a condition of an atmospheric equilibrium in the first liquid tank 61, the bubbles with the diameters of about 1–2 mm contained in the mixed liquid passing through the Y-character shape mixer 66 can not pass through the filter 69 and released in the atmosphere. As the filter 69, there can be used, for example a resin, such as Teflon and nylon; cloth, such as a cotton cloth; and paper, such as a filter paper.

Since the bubbles and precipitated salts and the like vary in the sizes and easiness of accumulation, it is difficult to remove them by one removing process. However, the bubbles and precipitated salts and the like can be surely removed through the two-step treating process including the first and second liquid tanks 61, 67. In case the bubbles and precipitated salts and the like are not fully removed from the mixed liquid and the mixed liquid is fed to the flow cell 27, light is scattered by the bubbles, so that the amount of transmitted light can not be accurately measured; while the precipitated salts and the like adhere to the wall surfaces of the flow cell 27, which results in reduction of the amount of transmitted light to cause drifts and reduction of sensitivity in the long run. As a result, the measuring accuracy is deteriorated. However, in the present embodiment, since the bubbles and precipitated salts and the like are sufficiently removed, the above mentioned problems can be solved and the measuring accuracy can be improved.

Further, a concrete structure of the apparatus according to the invention can be changed provided that it does not exceed the scope of the present invention. For example, although one tube was used for introducing each of the strong acidic liquid and the strong alkaline liquid to be measured, two tubes for the strong acidic liquid and three tubes for the strong alkaline liquid may be employed, or the tubes of different diameters may be used.

Although the squeezing pump 23 was used as an absorption system of the liquids in the above embodiment, a different absorption device, such as an air pump, aspirator and diaphragm valve, may be used. Also, the absorption device may be disposed in front of the flow cell 27 as shown in FIG. 1, or may be installed behind the flow cell 27, not shown.

As the optical filters 34, 35 and 52, a variety of types of filters can be used. For example, as the optical filter 35, an interference filter having a main transmitting wavelength of 400 nm may be used; a band-pass filter, for example, B-430 glass-filter produced by Hoya Co., Ltd.; or a sharp cut-off filter, for example, L-42 produced by Hoya Co., Ltd., may be considered. Also, as the photocells 36, 37 and 53, in addition to the Si photocell, other photoelectric converters equivalent thereto, such as a photomultiplier, photocell and CdS cell, may be used. Further, it is possible to replace it with a combination of a monochromator using a grating and a line sensor, such as CCD and PDA, by combining an optical filter and a part of a detector.

With regard to the liquid mixing and introduction system as shown in FIG. 11, it may be possible to remove the bubbles and precipitates by merely taking the supernatant liquid in the second liquid tank 67 and passing through the absorption tube 68. Therefore, the filter 69 is not necessarily used.

As described hereinabove, according to the electrolyte producing apparatus of the present invention, since the strong alkaline liquid produced on the cathode side is used, it is not required to add a coloring reagent as in a colorimetry method. Therefore, maintenance of the apparatus, such as exchange or supplement of the coloring reagents, is not required, and an extra space for them can be eliminated. In the invention, the concentration of hypochlorous acid in the strong acidic liquid produced on the anode side can be monitored momentarily. Further, since the mixing ratio of the strong acidic liquid and the strong alkaline liquid is set such that the hypochlorous acid in the strong acidic liquid is sufficiently dissociated into ions, it is possible to obtain data showing an accurate concentration of hypochlorous acid in the strong acidic liquid produced on the anode side by correcting with a correcting factor corresponding to the mixing ratio of the strong acidic liquid and the strong alkaline liquid.

Also, many bubbles are contained in the strong acidic liquid and the strong alkaline liquid obtained through electrolysis, and the strong alkaline liquid contains impurities, such as precipitated salts, which deteriorate the measuring accuracy. However, in the process for taking out the strong acidic liquid and the strong alkaline liquid from the electrolytic vessel and mixing of the same to feed the mixture to the measuring system, the bubbles and impurities, such as precipitated salts, can be sufficiently removed, so that the measuring accuracy can be prevented from being deteriorated, to thereby improve the accuracy.

While the invention has been explained with reference to the specific embodiments of the invention, the explanation is illustrative and the invention is limited only by the appended claims.

What is claimed is:

1. An electrolyte producing apparatus comprising:

an electrolyzing device having an anode side and a cathode side for producing an acidic liquid on the anode side and an alkaline liquid on the cathode side through electrolyzing a basic liquid;

a mixing device connected to the electrolyzing device for mixing a part of the acidic liquid produced on the anode side and a part of the alkaline liquid produced on the cathode side, said mixing device having means for regulating amounts of the acidic liquid and the alkaline liquid to form a predetermined ratio of a mixture of the acidic and alkaline liquids such that hypochlorous acid contained in the acidic liquid is substantially completely dissociated into $H^+$ ion and hypochlorous acid ion in the mixture; and a measuring device including light ejecting means for ejecting light to the mixture, and light receiving means for receiving the light passing through the mixture to measure a light absorbance of the hypochlorous acid ion in the mixture in an area of wavelengths of about 260 nm to 330 nm.

2. An electrolyte producing apparatus according to claim 1, further comprising a photometric electric circuit having means for obtaining a correction factor corresponding to said predetermined ratio of the acidic liquid and alkaline liquid, and an operation device for receiving the correction factor and performing a dilution correction with respect to measured data of the light absorbance by using said correction factor.

3. An electrolyte producing apparatus according to claim 1, wherein said mixing device includes a first open-air liquid tank with two tanks into which said part of the acidic liquid and said part of the alkaline liquid are separately introduced; a second open-air liquid tank into which supernatant liquids of the respective tanks of the first open-air liquid tank are introduced; and a device for introducing a supernatant liquid of the second open-air liquid tank into said measuring device.

4. An electrolyte producing apparatus according to claim 1, wherein said basic liquid contains chlorine to produce hypochlorous acid.

5. An electrolyte producing apparatus according to claim 1, wherein said light receiving means includes at least two light receiving devices with optical filters different from each other to measure at least two different light absorbencies, and at least one beam splitter for providing the beam from the light ejecting means to the at least two light receiving devices.

6. An electrolyte producing apparatus according to claim 5, wherein said measuring means further includes a photometric electric circuit for converting detected signals received at the light receiving means into signals for light absorbance.

7. An electrolyte producing apparatus according to claim 1, wherein said means for regulating the amounts in the mixing device are valves connected to the anode side and the cathode side.

8. An electrolyte producing apparatus according to claim 7, wherein said valves are adjusted so that the mixture of the acidic and alkaline liquids has a pH value of at least 10.

* * * * *